United States Patent
Katane et al.

(10) Patent No.: US 6,882,422 B2
(45) Date of Patent: Apr. 19, 2005

(54) INSPECTION DEVICE FOR BODY TO BE INSPECTED AND INSPECTION DEVICE OF FOREIGN MATTERS IN LIQUID FILLED IN TRANSPARENT CONTAINER

(75) Inventors: Tadahiro Katane, Hitachiota (JP); Hiromi Yamazaki, Hitachiota (JP); Hirohisa Fukuda, Hitachi (JP)

(73) Assignee: Hitachi Engineering Co. Ltd., Ibaraki (JP)

(*) Notice: Subject to any disclaimer, the term of this patent is extended or adjusted under 35 U.S.C. 154(b) by 227 days.

(21) Appl. No.: 10/243,868

(22) Filed: Sep. 16, 2002

(65) Prior Publication Data

US 2003/0063281 A1 Apr. 3, 2003

(30) Foreign Application Priority Data

Sep. 28, 2001 (JP) .................................. 2001-301605

(51) Int. Cl.$^7$ .............................................. G01N 21/90
(52) U.S. Cl. ......................................................... 356/427
(58) Field of Search ................................. 356/426–428

(56) References Cited

U.S. PATENT DOCUMENTS

| | | |
|---|---|---|
| 3,528,544 A | 9/1970 | Noguchi et al. |
| 3,942,001 A | 3/1976 | O'Connor |
| 4,832,173 A | 5/1989 | Hattori et al. |
| 5,073,708 A * | 12/1991 | Matsumoto et al. .... 250/223 B |
| 5,523,560 A | 6/1996 | Manique et al. |
| 6,275,603 B1 | 8/2001 | Cronshaw et al. |

* cited by examiner

*Primary Examiner*—Gregory J. Toatley, Jr.
*Assistant Examiner*—Amanda Merlino
(74) *Attorney, Agent, or Firm*—Mattingly, Stanger, Malur & Brundidge, P.C.

(57) ABSTRACT

In an inspection device of possible foreign matters included in transparent containers (20), the transparent containers (20) are successively loaded through a loader rotor (11) on to respective rotatable stands (8) arranged along the circumference on an inspection rotor (1). Each of plural motors (M) mounted on the inspection rotor (1) is coupled to one or more of the rotatable stands (8) carrying each of the containers (20). Each of the motors (M) together with the concerned rotatable stands (8) and the container (20) carried thereon are individually rotated according to one of predetermined rotation patterns (P1, P2 and P3). A picture image of the container (20) is subsequently taken so as to inspect foreign matters possibly included in the liquid.

2 Claims, 4 Drawing Sheets

ACCELERATION AND DECELERATION PATTEN

INSPECTION DEVICE FOR BODY TO BE INSPECTED AND INSPECTION DEVICE OF FOREIGN MATTERS IN LIQUID FILLED IN TRANSPARENT CONTAINER

BACKGROUND OF THE INVENTION

1. Field of the Invention

The present invention relates to an inspection device for a body to be inspected such as mass produced containers and to an inspection device of foreign matters in liquid filled in a transparent container such as glass bottles and PET bottles.

2. Conventional Art

Such as glass bottles and plastic bottles (bodies to be inspected) in which liquid such as medicine, eutrophic medicine and refreshing drink is filled are successively produced in great amount through mass production process. An inspection of possible foreign matters included in the filled in liquid is indispensable. FIG. 4A shows schematically a conventional inspection device.

In FIG. 4A, a rotor 50 is provided for such inspection in which bodies 51 to be inspected are successively sent from another transportation line, are successively taken in and are caused to be rotated and suddenly stopped to perform the foreign matter inspection. The rotor 50 is provided with rotatable stands for loading the bodies to be inspected around the circumference thereof and the bodies 51 to be inspected are placed and held on the rotatable stands. At two angle positions in rotating direction of the rotor 50 two picture image taking means constituted respectively by a combination of a camera 52 and an illumination 54 and by another combination of camera 53 and illumination 55 are provided. Along the outer circumference of the rotor 50 two belt drive units 56 are provided, which are driven according to an acceleration and deceleration pattern shown in FIG. 4B, thereby, the bodies to be inspected are once rotated and then stopped, after such activation only the filled in liquid rotates and is agitated due to inertia force. During rotation of filled in liquid due to inertia force, foreign matters included in the filled in liquid can be easily observed. Accordingly, the picture image of the rotating filled in liquid is taken by the sensors 52 and 53 and the picture image taken is processed to perform inspection of foreign matters in the filled in liquid.

In the above conventional example, since the bodies to be inspected 51 are driven from external by a belt, an accurate control such as of acceleration and deceleration and rpm thereof was impossible. Further, the acceleration and deceleration pattern deviates from a target solid line to dotted lines as shown by in FIG. 4B depending on conditions and secular change and the reverse rotation of the bodies to be inspected was also difficult. Accordingly, the accuracy of the foreign matter inspection was limited.

SUMMARY OF THE INVENTION

An object of the present invention is to provide an inspection device which enables to rotate bodies to be inspected accurately in a variety of rotation patterns suitable for desired inspections.

Another object of the present is to provide an inspection device of foreign matters in liquid filled in a transparent (including semi-transparent) container such as glass containers and plastic containers, which causes a desirable relative movement and agitation of the content liquid in the container so as to permit accurate and effective inspection of possible foreign matters included in the container.

According to one aspect of the present invention, the present invention is achieved by an inspection device for a body to be inspected comprising: a transferring means which transfers bodies to be inspected representing inspection objects by successively loading the same on respective rotatable stands; motors mounted on the transferring means, each of which couples with one or plural rotatable stands; a motor control means which controls the motors so as to rotate the bodies to be inspected on the respective rotatable stands according to a predetermined rotation pattern prior to inspection of the same; and an inspection means which inspects the bodies to be inspected during or after rotation thereof.

Further, the above transferring means is either a rotor or a linear transportation line.

Further, according to another aspect of the present invention the present invention is achieved by an inspection device of foreign matters in liquid filled in a transparent container comprising: a rotor which successively loads transparent containers filled with liquid representing inspection objects on rotatable stands arranged in order around the circumference thereof and rotates for transferring the same; motors mounted on the rotor, each of which couples to one or plural consecutive rotatable stands; a motor control means which controls the motors so as to rotate the transparent containers load on the rotatable stands according to a predetermined rotation pattern prior to inspection thereof; a camera which takes picture images of the transparent containers during or after the rotation thereof by making use of reflection right or transmission right; and inspection means which performs inspection of foreign matters in liquid filled in the transparent containers based on the picture images taken by the camera.

Further, according to still another aspect of the present invention the present invention is achieved by an inspection device of foreign matters in liquid filled in a transparent container comprising: a rotor which successively loads transparent containers filled with liquid representing inspection objects on rotatable stands arranged in order around the circumference thereof and rotates for transferring the same; motors mounted on the rotor, each of which couples to one or plural consecutive rotatable stands; an angle detector which detects rotation angle of the rotor; plural cameras which are arranged at plural positions around the circumference of the rotor so as to permit picture image taking of the transparent containers passing thereby by making use of reflection right or transmission right; a setting means which sets a predetermined rotation pattern for the respective cameras; a motor control means which specifies a motor immediately before entering into the field of view of each camera according to the detected rotation angle of the angle detector and performs the rotation control for the respective motors immediately before entering into the field of view of each camera so as to rotate the respective transparent containers loaded on the respective rotatable stands according to the predetermined rotation pattern for each camera; a camera control means which causes each camera to take picture images of the transparent containers which enter into the field of view of each camera; and an inspection means which performs inspection of foreign matters in liquid contained in the transparent containers based on the picture images taken by each camera.

Still further, in the present invention the transparent container is a cylindrical bottle or plastic container.

According to a further aspect of the present invention, the present invention is achieved by an inspection device of a body to be inspected including a transparent container and fluid filled therein comprising: an inspection rotor onto which bodies to be inspected are successively loaded and from which bodies inspected are successively unloaded; rotatable stands arranged regularly along the circumference of the inspection rotor for receiving each of the bodies to be inspected; motors mounted on the inspection rotor, each being coupled to one or more of the rotatable stands for rotating the bodies to be inspected carried thereon; a first picture image taking unit including a camera and an illumination disposed at a first position defined by a first angle in the rotation space of the inspection rotor which permits a picture image taking of the bodies to be inspected carried on the inspection rotor; a second picture image taking unit including a camera and an illumination disposed at a second position defined by a second angle in the rotation space of the inspection rotor which permits a picture image taking of the bodies to be inspected carried on the inspection rotor; a motor control unit which, when each of the bodies to be inspected approaches the first position, causes to rotate the concerned motor according to a first rotation pattern so as to rotate the body to be inspected via the rotatable stand and, when each of the bodies to be inspected approaches the second position, causes to rotate the concerned motor according to a second rotation pattern so as to rotate the body to be inspected via the rotatable stand; and a picture image processing unit which causes to take a picture image of the body to be inspected just experienced the rotation according to the first rotation pattern with the first picture image taking unit, causes to take a picture image of the body to be inspected just experienced the rotation according to the second rotation pattern with the second picture image taking unit and processes the picture images taken.

Further, each of the motors is preferably connected with the motor control unit via a slip ring.

In the inspection device of foreign matters in liquid filled in a container according to the present invention which causes the container to rotate and stop, around the circumference of an inspection rotor rotatable stands are regularly arranged, which are respectively coupled to respective motors. Bodies to be inspected (container and content liquid) are successively loaded on the respective rotatable stands from a loader rotor. At three different angle positions in rotation direction around the inspection rotor combinations of cameras and illuminations are disposed. Rotation of the respective motors is independently controlled and after rotating the container and then stopping the same according to predetermined rotation patterns, the picture image of the liquid filled in the container are taken by respective cameras at respective angle positions to inspect foreign matters therein.

DESCRIPTION OF THE EMBODIMENT

Figure 1:
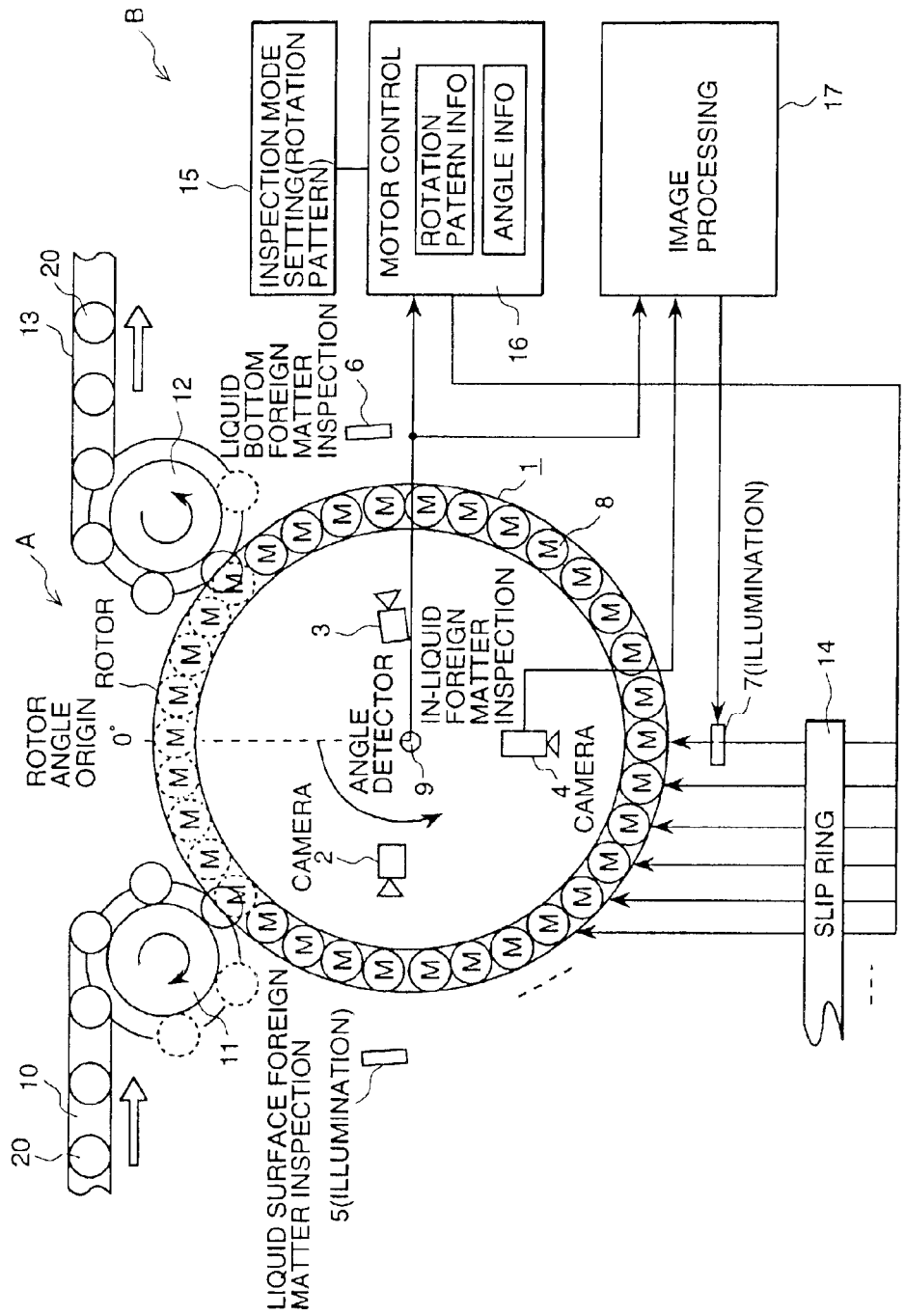
FIG. 1 is a schematic diagram showing an embodiment according to the present invention.

FIG. 1 is a diagram showing a transportation line system A for foreign matter inspection and a foreign matter inspection system B therefor. The transportation line system A for foreign matter inspection is constituted by a transportation lines 10 and 13, a loader rotor 11, a unloader rotor 12 and an inspection rotor 1. Bodies 20 to be inspected (such as transparent bottles and PET bottles in which liquid is filled) are successively carried in and loaded on the loader rotor 11, and the inspection rotor 1 receives these unloaded bodies and performs a predetermined inspection thereon. The unloader rotor 12 receives the bodies to be inspected after completing the inspection and sent out the same to the transportation line 13.

The inspection rotor 1 is a rotary body in which rotatable stands 8 for the bodies 20 to be inspected are arranged orderly and regularly around the circumference thereof and respective motors M are coupled to the respective rotatable stands 8 via the respective rotating shafts thereof, wherein the respective motor shafts can be either directly or indirectly coupled to the rotatable stands 8, and cameras 2, 3 and 4 are disposed at three predetermined positions around the circumference of the inspection rotor 1, and by making use of three illuminations each being disposed opposite to the corresponding camera picture images for foreign matter inspection are taken for the respective bodies 20 to be inspected placed on the respective rotatable stands 8 and passing between each pair of camera and illumination. A mechanism which holds each body 20 to be inspected on the rotatable stand 8 so as to permit rotation therewith is provided for each of the rotatable stands 8. Rotation of each motor M is controlled independently, and each motor M is designed to be provided a predetermined rotation pattern at every set angle position of the inspection rotor 1 and is controlled to rotate according to the predetermined rotation pattern. An angle detector 9 detects the rotation angle of the inspection rotor 1. The detected rotation angle is used for the rotation control of the motors M and the activation of the cameras and illuminations.

The foreign matter inspection system B is constituted by an inspection mode setting unit 15, a motor control unit 16, a picture image processing unit 17 and a slip ring 14 which performs relaying electrical signals for the motor control. The inspection mode setting unit 15 sets inspection items and provides a rotation pattern of the motors M corresponding to the set inspection item. The inspection items are set differently for the respective pairs of cameras and illuminations (2,5; 3,6; 4,7), for example, the combination of the camera 2 and the illumination 5 is used for a foreign matter inspection on liquid surface in the bodies 20 to be inspected, the combination of the camera 3 and the illumination 6 is used for a foreign matter inspection in liquid bottom in the bodies 20 to be inspected and the combination of the camera 4 and the illumination 7 is used for a foreign matter inspection in liquid in the bodies 20 to be inspected. Further, the inspection mode setting unit 15 determines and commands whether all of the inspection items are to be performed or whether some of the inspection items are to be omitted. Further, since it is possible to add other inspection items such as liquid level inspection as an optional item, the detection mode setting unit 15 can be designed to select the optional use inspection items.

The rotation patterns of the motors M corresponding to the inspection items are ones provided for the motor M which has just arrived immediately before the respective angle positions of the cameras 2, 3 and 4 (namely, positions immediately before inspections), and ones provided when forcedly rotate and stop the bodies 20 to be inspected which are held on the rotatable stands 8 coupled to the motors M concerned. The position (an offset value) immediately before the camera position is set in advance. Whether or not a body 20 to be inspected has arrived the immediately before the position can be determined by monitoring the detection value of the angle detector 9. Thereby, in order to detect foreign matters in liquid filled in the body 20 to be inspected, the body 20 to be inspected is at first rotated and then the rotation is suddenly stopped to cause only the content liquid to rotate in the container due to inertia force, thus possible foreign matters can be easily detected which are likely to move around in the content liquid. The moving around behavior of the foreign matters is utilized for easy detection thereof. In this instance, rpm (including normal and reverse rotation) and acceleration and deceleration pattern are determined depending on the inspection purposes and items. The rotation pattern is provided based on and in relation to the angle position of the inspection rotor 1.

The motor control unit 16 performs rotation control for respective motors M based on the rotation pattern information and the angle position information. The rotation control for the respective motors M is performed via the slip ring 14. The picture image processing unit 17 controls the cameras 2, 3 and 4 and the illuminations 5, 6 and 7 as well as captures the picture images taken by the cameras 2, 3 and 4 and processes the same to perform the foreign matter inspection. The control of the cameras 2, 3 and 4 and the illuminations 5, 6 and 7 is one for determining the picture taking timing. For example, the timing of an illumination ON and a camera ON. The contents of the picture image processing can be determined and prepared in a form of a software.

Figure 2:
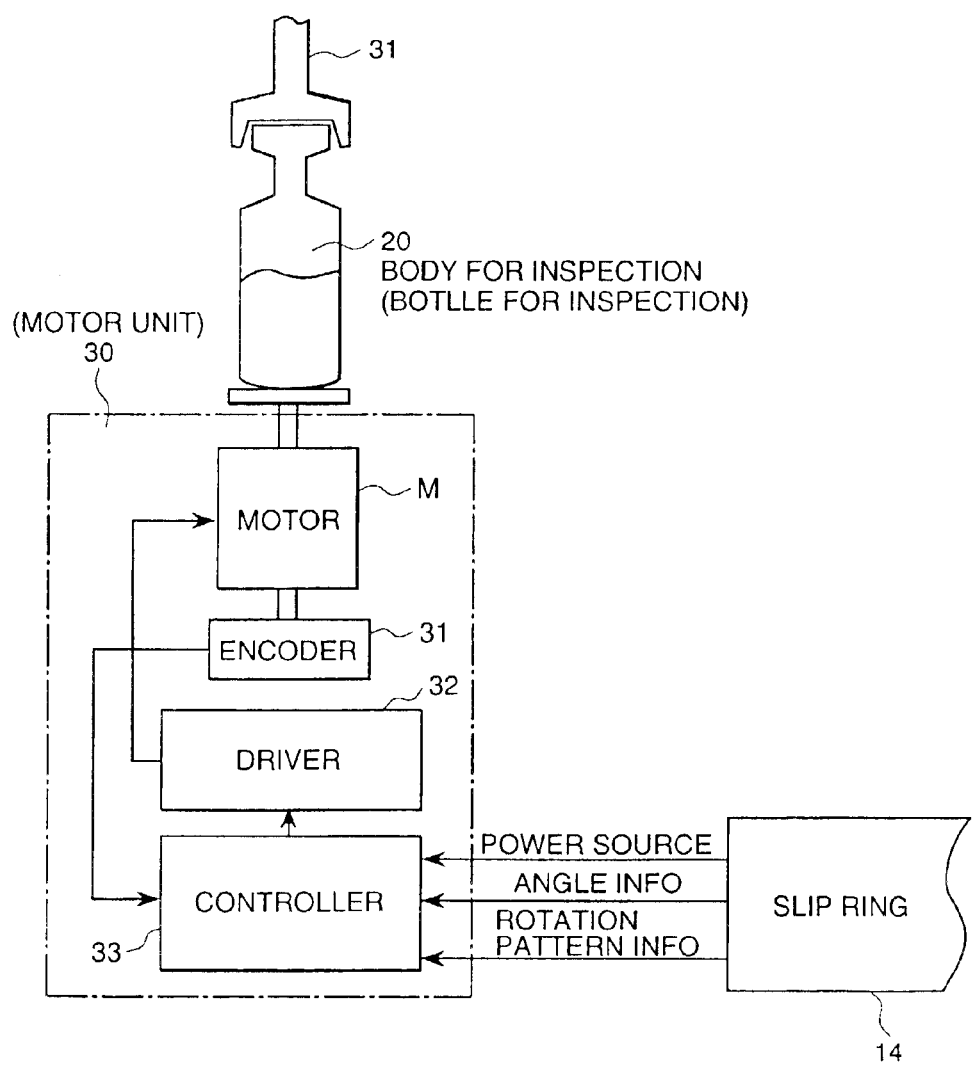
FIG. 2 is a schematic diagram of a motor unit including motor which rotates individual body to be inspected and a slip ring through which the motor unit is driven and controlled in the present invention.

FIG. 2 shows a structural diagram relating to a motor M. A body 20 to be inspected is placed on the rotatable stand 8 which is coupled to the rotating shaft of the motor M and the upper portion (for example, a cap of the inspection bottle) of the body 20 to be inspected is lightly held by a cup 31. The cup 31 is designed movable in up and down direction and when the body 20 to be inspected is placed on the rotatable stand 8 coupled to the motor M, the cup 31 moves down and holds lightly the upper portion of the body 20 to be inspected. Under the condition when the bodies 20 to be inspected are placed on the respective rotatable stands 8 on the inspection rotor 1, such holding state is maintained. When the body 20 to be inspected is carried toward the unloader rotor 12, the cup 31 moves up and the holding state is released.

During the light holding by the cup 31, the motor M is rotated and the body 20 to be inspected is caused to be rotated and suddenly stopped according to one of the set rotation patterns. For this purpose a motor unit 30 including the motor M is utilized. The motor unit 30 is constituted by an encoder 31, a driver unit 32 and a control unit 33. The encoder 31 detects rotation angle of the motor M and is used to check whether or not the motor rotate correctly by monitoring the detected rotation angle. The control unit 33 is supplied via the slip ring 14 a source power, angle information and rotation pattern information and performs rotation control of the motor M via the driver unit 32.

The inspection rotor 1 itself rotates while carrying the motors thereon, therefore, it is necessary to control the motors rotating together with the inspection rotor 1.

Plural motor units 30 are provided on the inspection rotor 1, therefore, information transmission lines corresponding to the number of motor units 30 which are separately controlled increase. Therefore, predetermined rotation patterns are sent to the respective motor units 30 in advance from the motor control unit 16, and during the inspection operation only angle information is continuously provided for all of the motor units 30, thereby, the respective motor units 30 are designed to perform self-control with respect to the respective motors concerned according to respective rotation patterns provided in advance.

Figure 3:
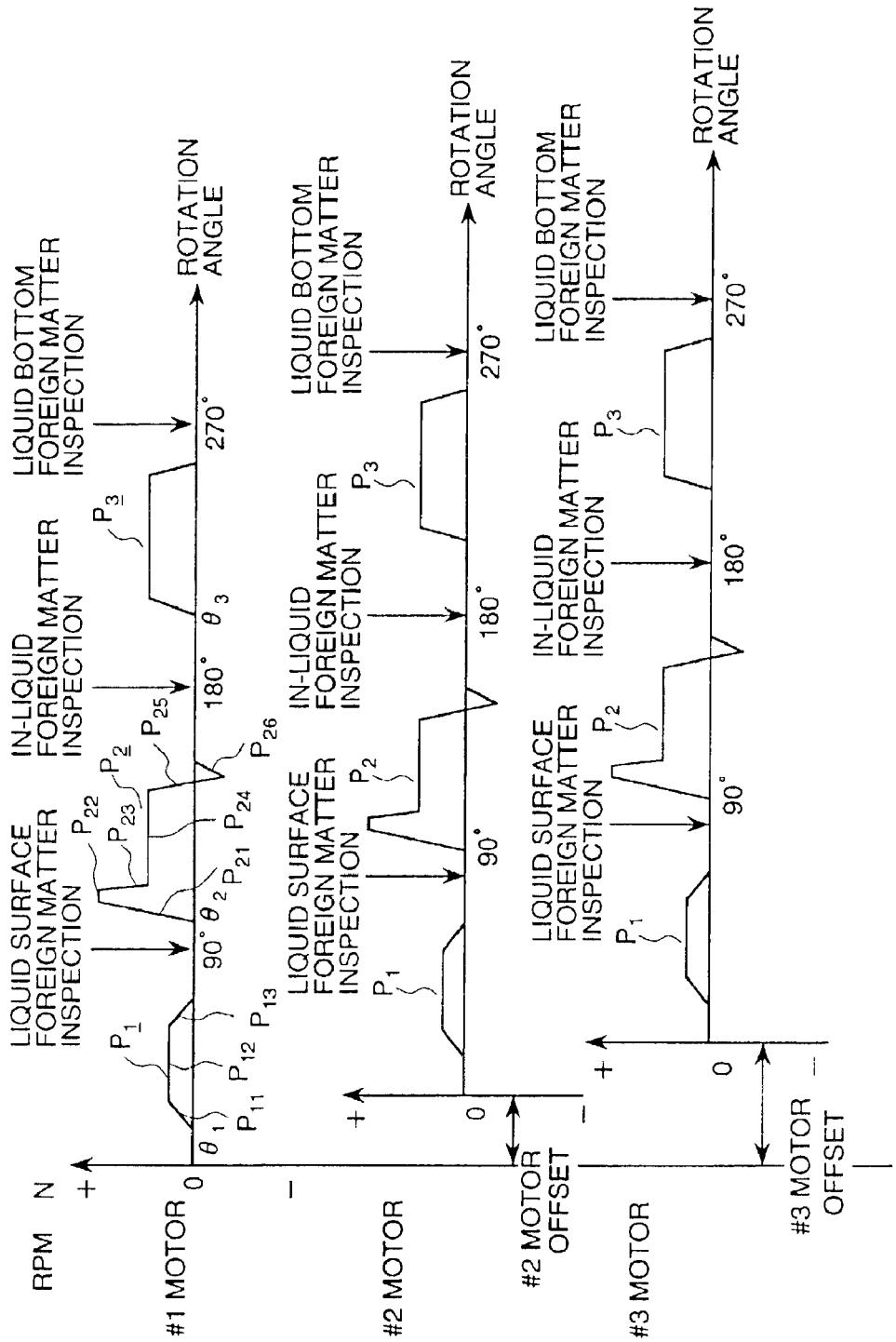
FIG. 3 is examples of rotation patterns according to which the motors according to the present embodiment are rotated.
Figure 4A:
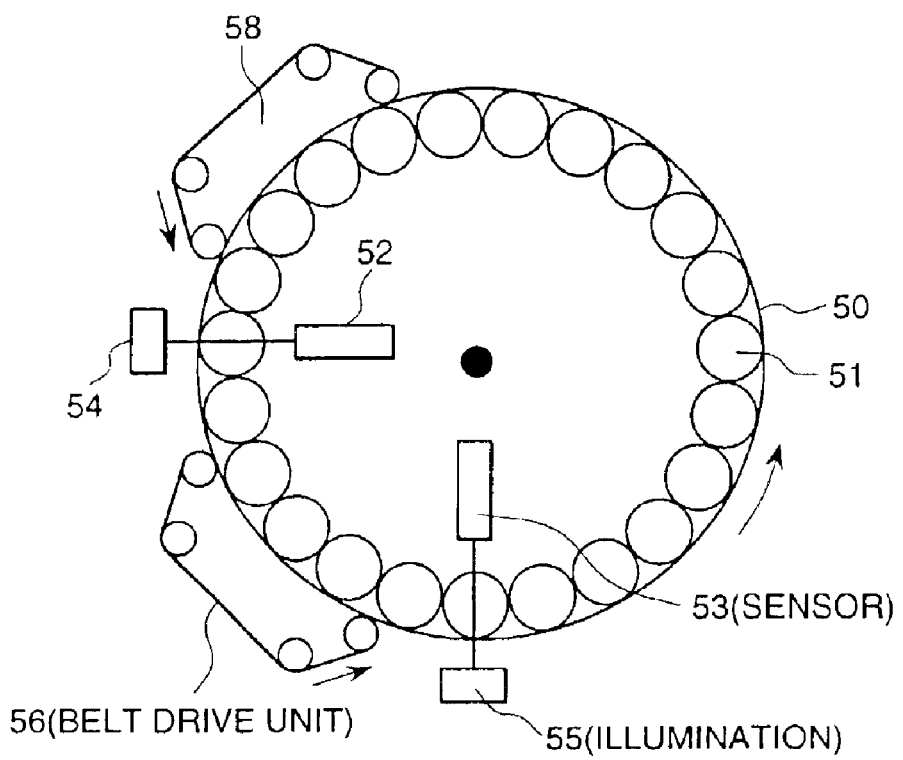
FIG. 4A is a schematic diagram of a conventional inspection device of foreign matters in liquid filled in a transparent container.
Figure 4B:
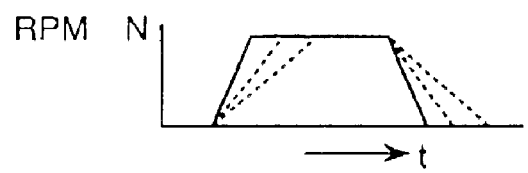
FIG. 4B shows an acceleration and declaration pattern used for rotating the respective containers on FIG. 4A device and shows a pattern deviation from a target pattern according to condition change.

FIG. 3 shows examples of the rotation patterns and illustrates those for three motors M identified as #1, #2 and #3 arranged consecutively. The rotation patterns for the motors #1, #2 and #3 are identical, but the initiation timing thereof is varied, in that offset of which timing difference represents the arrival time difference of the respective motors #1, #2 and #3 to the respective cameras 2, 3 and 4. In FIG. 3, the abscissa represents the angle position of the motors concerned on the inspection rotor 1 and the ordinate represents rpm of the motors. For the liquid surface foreign matter inspection with the camera 2 the rotation pattern P1 is used which includes an acceleration portion P11 rising up from angle $\theta_1$, a constant speed portion P12 having a predetermined value and a deceleration portion P13. The rotation pattern P2 is for an in-liquid foreign matter inspection and includes a rising-up portion P21 starting at angle $\theta_2$, a constant speed portion P22, a deceleration portion P23, another constant speed portion P24, another deceleration portion P25 and another acceleration portion P26. The negative rpm between the portions P25 and P26 shows a reverse direction drive of the body 20 to be inspection. The rotation pattern P3 is for a liquid bottom foreign matter inspection which is similar to the rotation pattern P1, but the predetermined value of the constant speed portion is determined high and the rising up and falling down rates thereof are determined slightly steep.

After rotating the respective concerned bodies 20 to be inspected and stopping the same suddenly according to the respective rotation patterns, picture images thereof are taken by the respective cameras 2, 3 and 4 for the predetermined inspections. Further, the angle in the abscissa represents angle position of the inspection rotor 1 from the reference point thereof (namely, the angle position of the concerned motor on the inspection rotor), and the angle is detected by the angle detector 9 and the detected angle is taken in the motor control unit 16 to detect the angles $\theta_1$, $\theta_2$ and $\theta_3$ and to perform the motor control according to the rotation patterns P1, P2 and P3.

The rotation patterns as shown in FIG. 3 are only examples, and depending on inspection purposes, shape of the body 20 to be inspected, kinds of liquid therein and kinds of foreign matters possibly included therein, a variety of rotation patterns can be set.

Now, modifications and application examples of the present invention will be explained.

(1) In the above embodiment one motor is coupled with one rotatable stand (rotary shaft). However, one motor can be coupled with more than one rotatable stands. For example, one motor can be designed to coupled two or four consecutive rotatable stands to drive and rotate the same at the same time.

(2) In the above embodiment, it is indicated that the rotation and stopping control of the concerned container is started immediately before the same enters into the field of view of the concerned camera. However, the moment of immediately before can be varied and it is sufficient if the liquid contained in the container is rotating due to inertia force when the same enters into the field of view of the concerned camera. The angles θ1, θ2 and θ3 and the offset value in FIG. 3 are not limited those illustrated. Further, it is indicated that the picture images are taken after rotating and stopping the concerned container, however, the picture images can be taken during rotation thereof.

(3) Instead of the inspection rotor as shown, a transportation line which moves linearly can be used.

(4) In the embodiment, each of the bodies to be inspected placed on the respective motor shafts (rotatable stands) is held through the cap thereof from upward. However, a holding structure can be integrated for each of the rotatable stands or the body to be inspected can be held from lateral direction.

(5) In the embodiment, it is indicated that the container is transparent. However, the container can be semi-transparent and it is sufficient, if picture images of foreign matters in the container can be taken by cameras with reflection or transmission light passing therethrough.

(6) In the embodiment, the inspection of foreign matters in liquid is exemplified. However, the present invention is applicable to a container being filled with fluid material instead of liquid and to an inspection of shape deformation of a container due to rotation, and the present invention covers all of the containers and the inspection objects which permits inspection thereof by rotating individually by making use of individual motors.

(7) Types of the motors used in the present invention include such as a stepping motor and a ultrasonic motor, but not limited thereto.

(8) In the present embodiment, the slip ring is used as the signal transmission means, however, other telecommunication means such as wireless and optical signal transmission can be used.

According to the present invention, since motors are individually provided for the respective rotatable stands, the rotation control and inspection of the respective containers loaded on the respective rotatable stands are enabled.

Further, according to the present invention, through accurate rotation and stopping of the containers, foreign matters possibly contained in liquid filled in the containers can be accurately inspected.

What is claimed is:

1. An inspection device of foreign matters in liquid filled in a transparent container comprising;

a rotor which successively loads transparent containers filled with liquid representing inspection objects on rotatable stands arranged in order around the circumference thereof and rotates for transferring the same;

motors mounted on the rotor, each of which couples to one or plural consecutive rotatable stands;

an angle detector which detects rotation angle of the rotor;

plural cameras which are arranged at plural positions around the circumference of the rotor so as to permit picture image taking of the transparent containers passing thereby by making use of reflection right or transmission right;

a setting means which sets a predetermined rotation pattern for the respective cameras;

a motor control means which specifies a motor immediately before entering into the field of view of each camera according to the detected rotation angle of the angle detector and performs the rotation control for the respective motors immediately before entering into the field of view of each camera so as to rotate the respective transparent containers loaded on the respective rotatable stands according to the predetermined rotation pattern set for each camera;

a camera control means which causes each camera to take picture images of the transparent containers which enter into the field of view of each camera; and an inspection means which performs inspection of foreign matters in liquid contained in the transparent containers based on the picture images taken by each camera.

2. An inspection device of foreign matters in liquid filled in a transparent container according to claim 1, wherein the transparent container is a cylindrical bottle or plastic container.

* * * * *